United States Patent [19]

Sugimori et al.

[11] Patent Number: 4,585,575
[45] Date of Patent: Apr. 29, 1986

[54] 2-SUBSTITUTED-6-(5-SUBSTITUTED-2-PYRIMIDINYL)NAPHTHALENES

[75] Inventors: Shigeru Sugimori, Fujisawashi; Toyoshiro Isoyama, Yokohamashi; Yasuyuki Goto, Yokohamashi; Tetsuya Ogawa, Yokohamashi, all of Japan

[73] Assignee: Chisso Corporation, Osaka, Japan

[21] Appl. No.: 683,162

[22] Filed: Dec. 18, 1984

[30] Foreign Application Priority Data

Jan. 11, 1984 [JP] Japan .................................. 59-3122

[51] Int. Cl.⁴ .......................... C09K 3/34; G02F 1/13; C07D 239/00; C07D 239/02
[52] U.S. Cl. .......................... 252/299.61; 252/299.5; 252/299.62; 350/350 R; 350/350 S; 544/242; 544/294; 544/335
[58] Field of Search ....................... 252/299.61, 299.62, 252/299.63, 299.5; 350/350 R, 350 S; 544/335, 294, 242

[56] References Cited

U.S. PATENT DOCUMENTS

| | | | |
|---|---|---|---|
| 3,997,536 | 12/1976 | Boller et al. | 252/299.61 |
| 4,062,798 | 12/1977 | Boller et al. | 252/299.61 |
| 4,386,007 | 5/1983 | Krause et al. | 252/299.62 |
| 4,402,849 | 9/1983 | Krause et al. | 252/299.62 |
| 4,432,885 | 2/1984 | Petrzilka et al. | 252/299.62 |
| 4,438,268 | 3/1984 | Zaschke et al. | 252/299.61 |
| 4,533,488 | 8/1985 | Fukui et al. | 252/299.61 |

FOREIGN PATENT DOCUMENTS

| | | | |
|---|---|---|---|
| 84194 | 7/1983 | European Pat. Off. | 252/299.61 |
| 2257588 | 6/1973 | Fed. Rep. of Germany | 252/299.61 |
| 160394 | 7/1983 | German Democratic Rep. | 252/299.61 |
| 1473990 | 5/1977 | United Kingdom | 252/299.61 |
| 2092169 | 8/1982 | United Kingdom | 252/299.61 |

OTHER PUBLICATIONS

Boller, A., et al., Mol. Cryst. Liq. Cryst., vol. 42, pp. 215–231 (1977).
Nash, J., et al., Mol. Cryst. Liq. Cryst., vol. 25, pp. 299–321 (1974).
Demus, A., et al., Flüssige Kristalle in Tabellen, Veb Deutscher Verlag für Grundstoffindustrie, Leipzig, pp. 234–269 (1974).
Zaschke, H., et al., Advances in Liquid Crystal Research & Appl., Bata, L. Pergamon Press, Oxford, pp. 1059–1074 (1981).
Zaschke, H., et al., Liquid Crystals & Ordered Fluids, vol. 4, Griffin, A., et al, Plenum Press, N.Y., pp. 75–87 (1984).

*Primary Examiner*—Teddy S. Gron
*Attorney, Agent, or Firm*—Leydig, Voit & Mayer, Ltd.

[57] ABSTRACT

Novel liquid crystal compounds having superior properties and liquid crystal compositions containing the same are provided, which compounds are expressed by the general formula

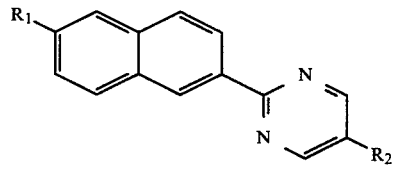

wherein $R_1$ represents an alkyl group or an alkoxy group, each having 1 to 10 carbon atoms and $R_2$ represents cyano group or an alkyl group having 1 to 10 carbon atoms.

17 Claims, No Drawings

2-SUBSTITUTED-6-(5-SUBSTITUTED-2-PYRIMIDINYL)NAPHTHALENES

BACKGROUND OF THE INVENTION

This invention relates to novel liquid crystal compounds and liquid crystal compositions containing the same.

Display elements utilizing liquid crystals have been generally used for watches, electric calculators, etc. These liquid crystal display elements utilize the optical anisotropy and dielectric anisotropy of liquid crystal substances, and the liquid crystal phases include nematic liquid crystal phases, smectic liquid crystal phases and cholesteric liquid crystal phases. However, among these, display elements utilizing nematic liquid crystals have been most generally pratically used. Namely, correspondingly to the electro-optical effect which has been applied to liquid crystal display, display elements are classified into TN (twisted nematic) type, DS (dynamic scattering) type, guest-host type, DAP type, etc., and the various properties required for liquid crystal substances used for these respective display elements. As for such liquid crystal substances, those which exhibit liquid crystal phases within a temperature range as broad as possible in the natural world are preferable. However, it is the present situation is such that there is no substance which alone satisfies the above conditions, but several kinds of liquid crystal substances are mixed with one another or with non-liquid crystal substances, for practical use. The above substances are required to be stable to moisture, heat, air, etc. and it is further required that the threshold voltage and saturation voltage necessary for driving display elements are as low as possible.

Further, liquid crystal compositions having a large value of optical anisotropy (hereinafter abbreviated to Δn) can inhibit occurrence of color unevenness due to a partial non-uniformity of the distance between substrates of liquid crystal display elements, to thereby reduce the distance between the substrates, which results in an advantage that it is possible to increase the intensity of an electric field even under the same impressed voltage. Thus, compounds having a large Δn are required.

The object of the present invention is to provide novel liquid crystal compounds suitable for such use applications.

SUMMARY OF THE INVENTION

The present invention resides in a first aspect as follows:

2-substituted-6-(5-substituted-2-pyrimidinyl)naphthalenes expressed by the general formula (I)

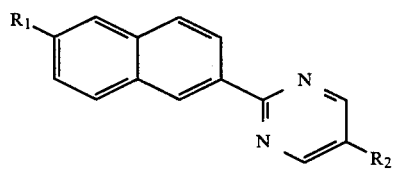

wherein $R_1$ represents an alkyl group or an alkoxy group each having 1 to 10 carbon atoms and $R_2$ represents a cyano group or an alkyl group having 1 to 10 carbon atoms.

Furthermore the present invention resides in a second aspect as follows:

liquid crystal compositions containing at least one kind of 2-substituted-6-(5-substituted-2-pyrimidinyl)-naphthalenes expressed by the above general formula (I).

DETAILED DESCRIPTION OF THE PREFERRED EMBODIMENTS

When the compounds of the present invention are added in a small amount to liquid crystal compositions prepared by mixing a number of other liquid crystal compounds such as esters, Schiff base compounds, biphenyls, phenylcyclohexanes, heterocyclic compounds, etc., it is possible to increase the Δn of the compositions and it is also possible to reduce the driving voltage of liquid crystal display elements utilizing the liquid crystal compositions.

The compounds of the present invention are prepared according to the following reactions:

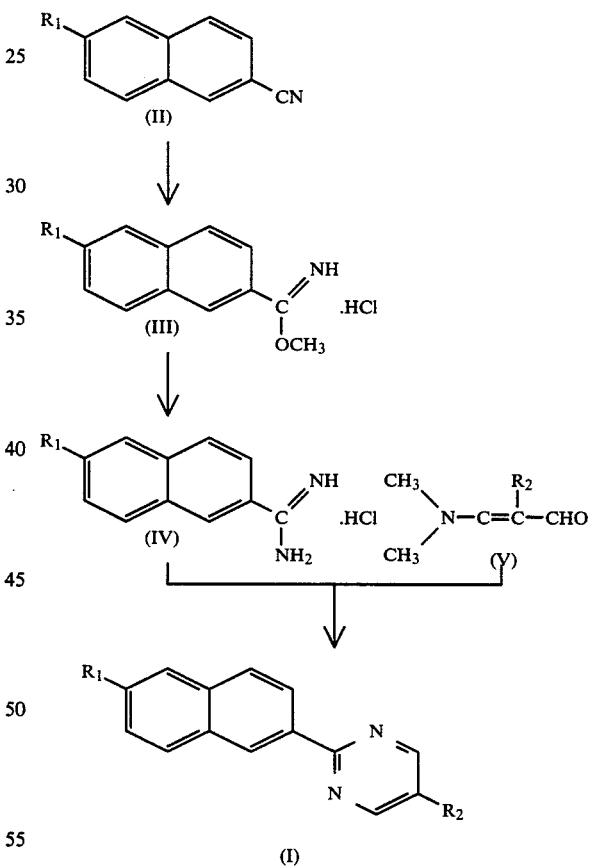

In these equations, $R_1$ and $R_2$ are as defined above.

First, a 6-substituted-2-naphthalenecarbonitrile (compound (II)) as a starting raw material is reacted with HCl gas and methanol to obtain an imidoether hydrochloride derivative (compound (III)), which is then reacted with $NH_3$ gas in an alcohol solvent to obtain an amidine hydrochloride derivative (compound (IV)). This compound (IV) and an acrolein derivative (V) are subjected to condensation-cyclization reaction in the presence of a suitable base catalyst (such as metal alcoholate, NaOH, 1,8-diazabicyclo[5.4.0]-7-undecene (DBU), triethylamine, pyridine, etc.) to obtain the objective compound (I).

Further, the liquid crystal compositions of the present invention are obtained by adding a small amount of 2-substituted-6-(5-substituted-2-pyrimidinyl)naphthalenes of the present invention to a mixture of compounds selected from liquid crystal compounds of esters, Schiff base compounds, biphenyls, phenylcyclohexanes, heterocyclic compounds, etc. The addition amount is in the range of 1 to 30% by weight, preferably 5 to 15% by weight.

Examples of ester liquid crystal compounds are 4-alkylphenyl trans-4-alkylcyclohexanecarboxylates, 4-alkoxyphenyl trans-4-alkylcyclohexanecarboxylates, 4-alkylphenyl 4-alkoxybenzoates, 4-cyanophenyl 4-alkylbenzoates, 4-cyanophenyl 4-(trans-4-alkylcyclohexyl)benzoates, etc. Examples of Schiff base liquid crystal compounds are 4-alkoxybenzylidene-4-alkanoyloxyanilines, 4-alkoxybenzylidene-4-alkylanilines, 4-alkoxybenzylidene-4-cyanoanilines, etc. Examples of biphenyl liquid crystal compounds are 4'-alkyl-4-cyanobiphenyls, 4'-alkoxy-4-cyanobiphenyls, 4'-alkoxy-4-alkylbiphenyls, etc. Examples of phenylcyclohexane liquid crystal compounds are trans-4-alkyl-(4-cyanophenyl)cyclohexanes, trans-4-alkyl-(4-alkoxyphenyl)cyclohexanes, etc. Examples of heterocyclic liquid crystal compounds are 5-alkyl-2-(4-cyanophenyl)-1,3-dioxanes, 5-alkyl-2-(4-cyanophenyl)pyrimidines, 5-cyano-2-(4-alkylphenyl)pyrimidines, etc.

The compositions of the present invention include for example, 70 to 99% by weight, preferably 85 to 95% by weight of one kind or a mixture of two to several kinds of trans-4-alkyl-(4-cyanophenyl)cyclohexanes and 1 to 30% by weight, preferably 5 to 15% by weight of 2-substituted-6-(5-substituted-2-pyrimidinyl)naphthalenes of the present invention. In another example, the compositions consist of 60 to 84% by weight, preferably 72 to 81% by weight of one kind or a mixture of two to several kinds of trans-4-alkyl-(4-cyanophenyl)cyclohexanes, 10 to 15% by weight, preferably 12 to 15% by weight of 4-(trans-4-alkyl)cyclohexyl-4'-cyanobiphenyls and 1 to 30% by weight, preferably 5 to 15% by weight of 2-substituted-6-(5-substituted-2-pyrimidinyl)naphthalenes of the present invention.

A concrete example of the above mixture of trans-4-alkyl-(4-cyanophenyl)cyclohexanes is a mixture of 20 to 35 parts by weight of a trans-4-propyl-(4-cyanophenyl)cyclohexane, 30 to 45 parts by weight of a trans-4-pentyl-(4-cyanophenyl)cyclohexane and 20 to 35 parts by weight of a trans-4-heptyl-(4-cyanophenyl)cyclohexane.

Examples of other alkyl substituents suitable for use in the above trans-4-alkyl-(4-cyanophenyl)cyclohexanes are methyl, ethyl, butyl, hexyl, octyl, nonyl, decyl, etc.

The present invention will be described in more detail by way of Examples.

EXAMPLE 1

2-Heptyl-6-(5-ethyl-2-pyrimidinyl)naphthalene

NaOH (1.1 g, 26 mmols) was added to anhydrous methanol (40 ml) and dissolved therein by heating to 60° C. with stirring. To the solution was added 6-heptyl-2-naphthalenecarboxamidine hydrochloride (4.0 g, 13 mmols) to prepare a suspension with stirring. To this suspension was dropwise added over one minute a solution obtained by dissolving α-ethyl-β-dimethylaminoacrolein (1.7 g, 13 mmols) in anhydrous methanol (5 ml), followed by gently refluxing the mixture with stirring for 2 hours, distilling off methanol under the atmospheric pressure after completion of the reaction, adding toluene (50 ml) to the residue to extract the resulting product, washing the extraction solution with a 2N-NaOH aqueous solution and then with water, drying over anhydrous sodium sulfate, and distilling off toluene under reduced pressure to obtain solids, which were then recrystallized from ethanol to obtain the objective 2-heptyl-6-(5-ethyl-2-pyrimidinyl)naphthalene (2.5 g, 7.8 mmols) (yield: 60%). M.P.: 62.3°–63.1° C.

EXAMPLES 2–8

Operations were carried out as in Example 1, using as raw materials, the corresponding 6-substituted-2-naphthalenecarboxamidine hydrochlorides and α-alkyl-β-dimethylaminoacroleins, to produce 2-heptyl-6-(5-butyl-2-pyrimidinyl)-naphthalene, 2-heptyl-6-(5-pentyl-2-pyrimidinyl)naphthalene, 2-heptyl-6-(5-hexyl-2-pyrimidinyl(naphthalene, 2-pentyloxy-6-(5-propyl-2-pyrimidinyl)naphthalene, 2-pentyloxy-6-(5-butyl-2-pyrimidinyl)naphthalene, 2-pentyloxy-6-(5-pentyl-2-pyrimidinyl)naphthalene and 2-pentyloxy-6-(5-hexyl-2-pyrimidinyl(naphthalene, respectively.

The values of physical properties of these compounds are shown in Table 1 together with the results of Example 1.

TABLE 1

|  | In formula (I) | | Phase transition point* (°C.) | | |
|---|---|---|---|---|---|
|  | $R_1$ | $R_2$ | C | N | I |
| Example 1 | $C_7H_{15}$ | $C_2H_5$ | 62.3~63.1 | | |
| Example 2 | $C_7H_{15}$ | $C_4H_9$ | 55.3~56.3 · (55.7~55.9) | | |
| Example 3 | $C_7H_{15}$ | $C_5H_{11}$ | 45.8~46.8 · 77.3~77.4 | | |
| Example 4 | $C_7H_{15}$ | $C_6H_{13}$ | 39.5~40.4 · 73.4~73.5 | | |
| Example 5 | $C_5H_{11}O$ | $C_3H_7$ | 103.8~104.5 · (98.2~98.3) | | |
| Example 6 | $C_5H_{11}O$ | $C_4H_9$ | 100.1~100.8 | | |
| Example 7 | $C_5H_{11}O$ | $C_5H_{11}$ | 113.8~114.4 · (99.2~99.3) | | |
| Example 8 | $C_5H_{11}O$ | $C_6H_{13}$ | 99.1~100.3 · (91.9~92.0) | | |

*C, N and I represent crystalline phase, nematic phase and isotropic liquid phase, respectively, and the symbol · in the lower column indicates that the phase in the upper column is present. The numeral figures in the parentheses represent monotropic transition points.

EXAMPLE 9

2-Heptyl-6-(5-cyano-2-pyrimidinyl)naphthalene

6-Heptyl-2-naphthalenecarboxamidine hydrochloride (4.0 g, 13 mmols), α-cyano-β-dimethylaminoacrolein (1.6 g, 13 mmols), triethylamine (30 ml) and pyridine (30 ml) were placed in a flask, followed by heating under reflux with stirring for 6 hours, cooling down to room temperature, and pouring the reaction mixture into water (500 ml) to deposit white solids, which were then separated by filtration and dissolved in toluene (100 ml), followed by washing the toluene layer with water, drying over anhydrous sodium sulfate and distilling off toluene under reduced pressure to obtain solids, which were recrystallized from a mixed solvent of ethanol-ethyl acetate (1:1) to obtain the objective 2-heptyl-6-(5-cyano-2-pyrimidinyl)naphthalene (3.0 g, 9.2 mmols) (yield: 70%). This product exhibited a liquid crystalline phase, and its crystalline-smectic phase transition point (C-S point) was 124.6°–125.6° C.; its smectic-nematic phase transition point (S-N point), 153.9°–154.1° C.; and its nematic-isotropic phase transition point (N-I point), 163.5°–163.7° C.

EXAMPLE 10

2-Pentyloxy-6-(5-cyano-2-pyrimidinyl)naphthalene

Operations were carried out as in Example 9 except that 6-heptyl-2-naphthalenecarboxamidine hydrochloride as a raw material was replaced by 6-pentyloxy-2-naphthalenecarboxamidine hydrochloride to produce 2-pentyloxy-6-(5-cyano-2-pyrimidinyl)naphthalene.

This product exhibited a liquid crystalline phase, and its crystalline-nematic phase transition point (C-N point) was 134.8°–135.5° C. and its N-I point was 190.9°–191.1° C.

EXAMPLE 11

(Application example 1)

A liquid crystal mixture (A) composed of trans-4-propyl-(4-cyanophenyl)cyclohexane: 24% by weight, trans-4-pentyl-(4-cyanophenyl)cyclohexane: 36% by weight, trans-4-heptyl-(4-cyanophenyl)cyclohexane: 25% by weight, and 4-(trans-4-pentyl)cyclohexyl-4'-cyanobiphenyl: 15% by weight, has a N-I point of 72.0° C., a dielectric anisotropy value (hereinafter abbreviated to $\Delta\epsilon$) of 11.6 and a $\Delta n$ of 0.140. Two substrates each having a stannic oxide transparent electrode, coated with silicon dioxide and subjected to rubbing treatment, were opposed to each other so as to give a distance between the electrodes, of 10 μm. The above liquid crystal mixture (A) was sealed between the thus provided substrates to prepare a liquid crystal cell, and its characteristics were measured at 20° C. to give a threshold voltage (hereinafter abbreviated to $V_{th}$) of 1.75 V and a saturation voltage (hereinafter abbreviated to $V_{sat}$) of 2.40 V.

A composition obtained by dissolving 15% by weight of 2-heptyl-6-(5-hexyl-2-pyrimidinyl)naphthalene prepared in Example 4 of the present invention in 85% by weight of the above liquid crystal mixture (A), had a N-I point of 72.2° and a dielectric anisotropy value of 11.0 and its $\Delta n$ increased to 0.146. Further, as to the characteristics of the same liquid crystal cell as the above using the composition, its $V_{th}$ and $V_{sat}$ lowered to 1.58 V and 2.17 V to a large extent, respectively.

EXAMPLE 12

(Application example 2)

A composition prepared by dissolving 15% by weight of 2-heptyl-6-(5-pentyl-2-pyrimidinyl)naphthalene prepared in Example 3 of the present invention in 85% by weight of the liquid crystal composition (A) used in Example 11, had a N-I point of 75.1° C. and a dielectric anisotropy value of 11.1, and its $\Delta n$ increased to 0.147. Further, as to the characteristics of the same liquid crystal cell as the above using the composition, its $V_{th}$ and $V_{sat}$ were 1.75 V and 2.26 V, respectively.

EXAMPLE 13

(Application example 3)

A composition prepared by dissolving 15% by weight of 2-pentyloxy-6-(5-propyl-2-pyrimidinyl)naphthalene prepared in Example 5 of the present invention in 85% by weight of the above liquid crystal mixture (A) had a N-I point of 77.6° C. and a dielectric anisotropy value of 11.4, and its $\Delta n$ increased to 0.149. As to the characteristics of the same liquid crystal cell as the above using the composition, its $V_{th}$ and $V_{sat}$ lowered to 1.70 V and 2.21 V to a large extent, respectively.

EXAMPLE 14

(Application example 4)

A liquid crystal mixture (B) composed of trans-4-propyl-(4-cyanophenyl)cyclohexane: 30% by weight, trans-4-pentyl-(4-cyanophenyl)cyclohexane: 40% by weight, and trans-4-heptyl-(4-cyanophenyl)cyclohexane: 30% by weight, has a N-I point of 52.1° C., a $\Delta\epsilon$ of 11.2 and a $\Delta n$ of 0.119. The above liquid crystal mixture (B) was sealed in the same liquid crystal cell as that used in Example 11, to measure its characteristics at 20° C. Its $V_{th}$ and $V_{sat}$ were 1.54 V and 2.13 V, respectively.

A composition prepared by dissolving 10% by weight of 2-heptyl-6-(5-cyano-2-pyrimidinyl)naphthalene in 90% by weight of the above liquid crystal mixture (B), had a N-I point of 61.2° C., a $\Delta\epsilon$ of 10.9 and a $\Delta n$ of 0.138. Further, as to the characteristics of the same liquid crystal cell as the above using the composition, its $V_{th}$ and $V_{sat}$ were 1.52 V and 2.10 V, respectively.

What we claim is:

1. A 2-substituted-6-(5-substituted-2-pyrimidinyl)naphthalene expressed by the general formula

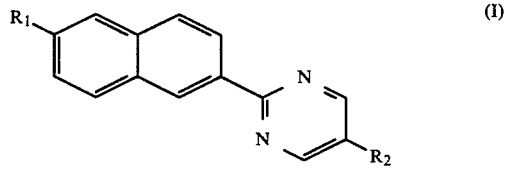

(I)

wherein $R_1$ represents an alkyl group or an alkoxy group, each having 1 to 10 carbon atoms and $R_1$ represents cyano group or an alkyl group having 1 to 10 carbon atoms.

2. A 2-alkyl-6-(5-alkyl-2-pyrimidinyl)naphthalene according to claim 1 wherein said $R_1$ and $R_2$ in the general formula (I) each represents an alkyl group having 1 to 10 carbon atoms.

3. A 2-alkoxy-6-(5-alkyl-2-pyrimidinyl)naphthalene according to claim 1 wherein said $R_1$ in the general formula (I) represents an alkoxy group having 1 to 10 carbon atoms and said $R_2$ therein represents an alkyl group having 1 to 10 carbon atoms.

4. A 2-alkyl-6-(5-cyano-2-pyrimidinyl)naphthalene according to claim 1 wherein said $R_1$ in the general formula (I) represents an alkyl group having 1 to 10 carbon atoms and said $R_2$ therein represents cyano group.

5. A 2-alkoxy-6-(5-cyano-2-pyrimidinyl)naphthalene according to claim 1 wherein said $R_1$ in the general formula (I) represents an alkoxy group having 1 to 10 carbon atoms and said $R_2$ therein represents cyano group.

6. Liquid crystal compositions containing at least one 2-substituted-6-(5-substituted-2-pyrimidinyl)naphthalene expressed by the general formula (I) of claim 1.

7. Liquid crystal compositions according to claim 6 wherein said at least one 2-substituted-6-(5-substituted-2-pyrimidinyl)naphthalene is contained in an amount of 1 to 30% by weight in said liquid crystal compositions.

8. The 2-alkyl-6-(5-alkyl-2-pyrimidinyl)naphthalene according to claim 2 wherein $R_1$ is $C_7H_{15}$ and $R_2$ is $C_2H_5$.

9. The 2-alkyl-6-(5-alkyl-2-pyrimidinyl)naphthalene according to claim 2 wherein $R_1$ is $C_7H_{15}$ and $R_2$ is $C_4H_9$.

10. The 2-alkyl-6-(5-alkyl-2-pyrimidinyl)naphthalene according to claim 2 wherein $R_1$ is $C_7H_{15}$ and $R_2$ is $C_5H_{11}$.

11. The 2-alkyl-6-(5-alkyl-2-pyrimidinyl)naphthalene according to claim 2 wherein $R_1$ is $C_7H_{15}$ and $R_2$ is $C_6H_{13}$.

12. The 2-alkoxy-6-(5-alkyl-2-pyrimidinyl)naphthalene according to claim 3 wherein $R_1$ is $C_5H_{11}O$ and $R_2$ is $C_3H_7$.

13. The 2-alkoxy-6-(5-alkyl-2-pyrimidinyl)naphthalene according to claim 3 wherein $R_1$ is $C_5H_{11}O$ and $R_2$ is $C_4H_9$.

14. The 2-alkoxy-6-(5-alkyl-2-pyrimidinyl)naphthalene according to claim 3 wherein $R_1$ is $C_5H_{11}O$ and $R_2$ is $C_5H_{11}$.

15. The 2-alkoxy-6-(5-alkyl-2-pyrimidinyl)naphthalene according to claim 3 wherein $R_1$ is $C_5H_{11}O$ and $R_2$ is $C_6H_{13}$.

16. The 2-alkyl-6-(5-cyano-2-pyrimidinyl)naphthalene according to claim 4 wherein $R_1$ is $C_7H_{15}$.

17. The 2-alkoxy-6-(5-cyano-2-pyrimidinyl)naphthalene according to claim 5 wherein $R_1$ is $C_5H_{11}O$.

* * * * *